United States Patent
Kawano et al.

(10) Patent No.: US 7,176,428 B2
(45) Date of Patent: Feb. 13, 2007

(54) LASER-BASED, MULTIPHOTON-EXCITATION-TYPE OPTICAL EXAMINATION APPARATUS

(75) Inventors: Yoshihiro Kawano, Hachioji (JP); Tadashi Hirata, Hachioji (JP); Tatsuo Nakata, Hino (JP); Hiroshi Sasaki, Nerima-ku (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/070,191

(22) Filed: Mar. 3, 2005

(65) Prior Publication Data

US 2005/0279950 A1    Dec. 22, 2005

(30) Foreign Application Priority Data

Mar. 12, 2004  (JP) ............................ 2004-070198
Mar. 12, 2004  (JP) ............................ 2004-070268

(51) Int. Cl.
*G02B 7/04* (2006.01)
*H01J 3/14* (2006.01)
*H04B 10/12* (2006.01)

(52) U.S. Cl. .................... 250/201.3; 250/216; 398/147

(58) Field of Classification Search ............ 250/201.3, 250/216, 227.21, 227.11; 398/45, 48, 55, 398/56, 81, 91, 147, 158, 38, 33, 192, 195, 398/196, 197, 95; 385/27, 28, 37
See application file for complete search history.

(56) References Cited

U.S. PATENT DOCUMENTS

| 5,995,281 | A * | 11/1999 | Simon et al. ............... 359/368 |
| 6,316,153 | B1 * | 11/2001 | Goodman et al. ............ 430/8 |
| 6,337,660 | B1 * | 1/2002 | Esman et al. ............... 342/375 |
| 6,445,862 | B1 * | 9/2002 | Fajardo et al. .............. 385/125 |
| 6,449,039 | B1 * | 9/2002 | Bouzid ....................... 356/318 |
| 6,485,413 | B1 * | 11/2002 | Boppart et al. ............. 600/160 |
| 2002/0024015 | A1 * | 2/2002 | Hoffmann et al. .......... 250/311 |
| 2002/0154398 | A1 * | 10/2002 | Wolleschensky et al. ... 359/385 |
| 2003/0107815 | A1 * | 6/2003 | Redmond ................... 359/619 |
| 2004/0207850 | A1 * | 10/2004 | Kwak et al. ................ 356/432 |

FOREIGN PATENT DOCUMENTS

JP    2002-243641    8/2002

* cited by examiner

*Primary Examiner*—Georgia Epps
*Assistant Examiner*—Pascal M. Bui-Pho
(74) *Attorney, Agent, or Firm*—Kenyon & Kenyon LLP

(57) ABSTRACT

The invention provides a multiphoton-excitation-type examination apparatus that efficiently generates a multiphoton-excitation effect, that makes the measurement head compact, and that can be easily adjusted when the measurement head is replaced. The multiphoton-excitation-type examination apparatus comprises a laser light source that oscillates ultrashort pulsed laser light; an optical fiber that transmits the ultrashort pulsed laser light from the laser light source; a support member; a measurement head supported on the support member so as to be movable upwards and downwards and at an angle, and having an optical system that irradiates a specimen with the ultrashort pulsed laser light transmitted by the optical fiber that measures fluorescence or reflected light coming from the specimen; and a dispersion-compensating member, in the measurement head, that compensates for group velocity dispersion of the ultrashort pulsed laser light irradiated onto the specimen.

15 Claims, 11 Drawing Sheets

LASER-BASED, MULTIPHOTON-EXCITATION-TYPE OPTICAL EXAMINATION APPARATUS

BACKGROUND OF THE INVENTION

1. Field of the Invention

The present invention relates to a multiphoton-excitation-type examination apparatus.

2. Description of Related Art

One example of a conventional apparatus for observing the function of cells and the like by irradiating a biological specimen with excitation light from the surface thereof and detecting the fluorescence produced from a comparatively deep location below the surface of the specimen is a multiphoton-excitation-type microscope (for example, see Japanese Unexamined Patent Application Publication No. 2002-243641, page 3 etc.).

This multiphoton-excitation-type microscope uses an ultrashort pulsed laser as a laser light source to emit ultrashort pulses. It is known that the pulse width of ultrashort laser pulses increases due to group velocity dispersion upon passing through optical components, such as optical fibers, lenses in optical devices, and the like.

Accordingly, a technique has been disclosed in which a so-called pulse stretcher, composed of a prism, is disposed at the input face of an optical fiber to lengthen the pulse width, so that the pulses are introduced into the optical fiber with the peak power of each pulse reduced, and a pulse compressor is disposed at the output face of the optical fiber to introduce the light to an optical device after compressing the pulse length to at least the length when the laser light was emitted. By doing so, when the light is irradiated onto a specimen from an objective lens, the pulse width can be made close to the original pulse width of the laser light.

However, the measurement head, which irradiates the specimen with laser light and detects fluorescence or reflected light obtained therefrom, should be made more compact from the viewpoint of the need to carry out measurement from any angle and position with respect to the examination site in a small laboratory animal or the like. Accordingly, the structure disclosed in Japanese Unexamined Patent Application Publication No. 2002-243641 suffers from the drawback that it is not possible to reduce the size of the measurement head. Also, if it is necessary to use different optical systems depending on the measurement site, the need for a small measurement head that can be exchanged should be considered. In such a case, since a pulse stretcher and pulse compressor are disposed outside the measurement head, as in the conventional art, there is a drawback in that adjustment of the pulse stretcher and pulse compressor must be carried out each time the measurement head is exchanged. Also, since the pulse stretcher and pulse compressor are disposed outside the laser light source, the optical fiber, and the measurement head, as in the conventional art, there is another drawback in that the overall size of the apparatus becomes large.

BRIEF SUMMARY OF THE INVENTION

In light of the circumstances described above, an object of the present invention is to provide a multiphoton-excitation-type examination apparatus that can efficiently generate a multiphoton-excitation effect, that can be made compact, and that can be easily adjusted when the measurement head is exchanged. Also, another object of the present invention is to provide a multiphoton-excitation-type examination apparatus that can efficiently generate the multiphoton-excitation effect and that realize a compact measurement head and overall apparatus the smallest possible structure.

In order to achieve the above-described object, the present invention provides the following solutions.

According to a first aspect, the present invention provides a multiphoton-excitation-type examination apparatus including a laser light source that oscillates ultrashort pulsed laser light; an optical fiber that transmits the ultrashort pulsed laser light from the laser light source; a support member; a measurement head supported on the support member so as to be movable upwards and downwards and at an angle, and having an optical system that irradiates a specimen with the ultrashort pulsed laser light transmitted by the optical fiber that measures fluorescence or reflected light coming from the specimen; and a dispersion-compensating member, in the measurement head, that compensates for group velocity dispersion of the ultrashort pulsed laser light irradiated onto the specimen.

According to this aspect, since the measurement head is separated from the laser light source and is connected thereto by the optical fiber, the measurement head can be made more compact and can be set at any angle and position with respect to the specimen by bending the optical fiber. Accordingly, it is possible to carry out measurement by positioning the measurement head according to the shape of the specimen and the examination site.

The ultrashort pulsed laser light emitted from the laser light source experience positive group velocity dispersion while passing through the optical fiber and the optical elements inside the measurement head, which lengthens the pulse width. On the other hand, by making the ultrashort pulsed laser light introduced into the measurement head pass through the dispersion-compensating member, the group velocity dispersion is compensated for, and is irradiated onto the specimen as ultrashort pulsed laser light having the same pulse width at that originally emitted from the laser light source. Accordingly, sufficient power can be applied to a predetermined position deep inside the specimen, which efficiently produces a multiphoton-excitation effect and allows detailed fluorescence images of a site deep inside the specimen to be acquired.

In the aspect of the invention described above, the measurement head and the optical fiber are preferably connected in a detachable manner. Since the dispersion-compensating element is provided in the measurement head, even if the measurement head is separated from the optical fiber and replaced with another measurement head having different optical elements according to the object to be measured, the total group velocity dispersion can be suppressed, and it is possible to efficiently generate the multiphoton-excitation effect.

The aspect of the invention described above may also include an optical scanning unit, in the measurement head, that scans the ultrashort pulsed laser light transmitted by the optical fiber onto the specimen. In this case, the dispersion-compensating member is disposed between an end of the optical fiber and the optical scanning unit.

By operating the optical scanning unit, it is possible to scan the ultrashort pulsed laser light on the specimen, which allows measurement of a one-dimensionally or two-dimensionally wide region using the multiphoton-excitation effect. In such a case, by disposing the dispersion-compensating member between the end of the optical fiber and the optical scanning unit, it is possible to compensate for the group velocity dispersion experienced by the ultrashort pulsed laser light before the optical path is changed by the optical scanning unit.

In the aspect of the invention described above, the dispersion-compensating member may be exchangeable.

With this configuration, it is possible to efficiently generate the multiphoton-excitation effect by exchanging it with a dispersion-compensating member that can compensate for the total group velocity dispersion, even if the laser light source is exchanged or if the optical fiber is exchanged.

The aspect of the invention described above may also include an adjustment mechanism that adjusts the amount of dispersion-compensation of the dispersion-compensating member.

With this configuration, since the amount of dispersion compensation is adjusted by operating the adjustment mechanism, it is possible to irradiate the specimen with ultrashort pulsed laser light whose group velocity dispersion has been effectively compensated according to the overall change in group velocity dispersion due to exchanging the laser light source and the optical fiber.

In the aspect of the invention described above, the dispersion-compensating member may be formed of a dispersion-compensating mirror that imparts negative group velocity dispersion.

With the dispersion-compensating mirror, since it is possible to compensate for the group velocity dispersion simply by reflecting the ultrashort pulsed laser light supplied from the optical fiber, the structure can simplified and it is possible to reduce the size of the measurement head.

In this case, a dispersion-imparting member that imparts positive group velocity dispersion to the light introduced into the optical fiber may be disposed between the laser light source and the optical fiber.

By doing so, group velocity dispersion can be imparted to the ultrashort pulsed laser light emitted from the laser light source and light whose pulse width is lengthened can be introduced into the optical fiber. Accordingly, the peak power of the ultrashort pulsed laser light can be reduced, which allows nonlinear effects in the fiber to be suppressed, and also makes it possible to reduce the damage caused to the optical fiber. Also, by compensating for the group velocity dispersion of the ultrashort pulsed laser light emitted from the optical fiber, which has a large amount of group velocity dispersion imparted thereto, using the dispersion-compensating mirror, it is possible to irradiate the specimen with ultrashort pulsed laser light whose pulse width is as short as that emitted by the laser light source.

Also, the dispersion-imparting member may be an acousto-optical device.

Using the acousto-optical device, positive group velocity dispersion can easily be imparted to the light, which allows the pulse width to be lengthened. Also, intensity adjustment and wavelength selection of the irradiation light can be carried out at high speed.

The aspect of the invention described above may also include a first dispersion-imparting member, disposed between the laser light source and the optical fiber, that imparts negative group velocity to the light introduced into the optical fiber. In this case, the dispersion-compensating member is formed of a second dispersion-imparting member that imparts positive group velocity dispersion.

With this configuration, the ultrashort pulsed laser light emitted from the laser light source can be introduced into the optical fiber after having negative group velocity dispersion imparted thereto by means of the first dispersion-imparting member. By imparting negative group velocity dispersion, the pulse width can be sufficiently lengthened, which allows the peak power of the ultrashort pulsed laser light to be reduced, thereby suppressing nonlinear effects in the optical fiber, and therefore, it is possible to maintain the integrity of the optical fiber. Furthermore, since positive group velocity dispersion is imparted to the ultrashort pulsed laser light by passing it through the second dispersion-imparting member, it is possible to irradiate the specimen with ultrashort pulsed laser light having the original pulse width by matching the positive group velocity dispersion due to the optical fiber and the optical elements.

In this case, it is effective if the second dispersion-imparting member is formed of zinc selenide or tellurium oxide crystal.

By using such crystals, since sufficient compensation of the group velocity dispersion can be carried out in a small volume, there is an advantage in that it is possible to reduce the size of the measurement head and improve its ease of use.

The aspect of the invention described above may also include an objective unit, disposed opposite the specimen, that is detachable from and attachable to the measurement head; and an objective dispersion-compensating unit, disposed in the objective unit, that compensates for the group velocity dispersion of the ultrashort pulsed laser light inside the objective unit.

With this configuration, suitable compensation of the group velocity dispersion of the objective optical system can be achieved by operating the objective dispersion-compensating unit. Therefore, even if the objective unit attached to the measurement head is replaced with another objective unit having an optical system with different magnification and so on, the group velocity dispersion can be suitable compensated for, which allows the multiphoton-excitation effect to be realized efficiently.

According to a second aspect, the present invention provides a multiphoton-excitation-type examination apparatus including a laser light source that oscillates ultrashort pulsed laser light; an optical fiber unit that transmits the ultrashort pulsed laser light from the laser light source; and a measurement head having an optical system that irradiates a specimen with the ultrashort pulsed laser light transmitted by the optical fiber unit and that measures fluorescence or reflected light coming from the specimen. The optical fiber unit includes an optical fiber that imparts negative group velocity dispersion.

According to this aspect of the invention, since the measurement head is separated from the laser light source and is connected thereto by the optical fiber unit, the measurement head can be made compact and can be set at any angle and position with respect to the specimen by bending the optical fiber constituting the optical fiber unit. Accordingly, it is possible to perform measurement with the measurement head positioned according to the shape of the specimen and the examination site.

The ultrashort pulsed laser light emitted from the laser light source experiences positive group velocity dispersion while passing through the collimator lens provided inside the laser light source and the optical elements inside the measurement head, which lengthens the pulse width. On the other hand, since negative group velocity dispersion is imparted by passing through the optical fiber, the group velocity dispersion due to the other optical elements is compensated for, and the light is irradiated onto the specimen as ultrashort pulsed laser light having the same pulse width at that originally emitted from the laser light source. Accordingly, sufficient power can be applied to a predetermined position deep inside the specimen, which efficiently produces a multiphoton-excitation effect and allows detailed fluorescence images of a site deep inside the specimen to be acquired.

In this case, since dispersion compensation is carried out with the optical fiber in this aspect of the invention, there is an advantage in that it is not necessary to provide a specially designed dispersion-compensating device. In other words, when carrying out dispersion compensation, it has been necessary to use a large, complex device, such as a XXXX, which uses two prisms disposed with a spacing therebetween; however, with this aspect of the invention, dispersion compensation is carried out using the optical fiber unit itself, which guides the ultrashort pulsed laser light from the light source to the measurement head, thus allowing the configuration to be made more compact.

In the aspect of the invention described above, the optical fiber is preferably a photonic-crystal fiber. With a photonic-crystal fiber, since a plurality of types of element having different amounts of group velocity dispersion are used, depending on the wavelength of the ultrashort pulsed laser light transmitted therethrough, it is possible to select an element exhibiting negative group velocity dispersion, depending on the wavelength of the ultrashort pulsed laser light used, which allows the object described above to be realized.

In the aspect of the invention described above, the laser light source is capable of changing the wavelength of the emitted ultrashort pulsed laser light. In addition, the optical fiber means includes a plurality of optical fibers having different amounts of group velocity dispersion; and a fiber switching unit that selects one of the optical fibers to transmit the ultrashort pulsed laser light based on the wavelength of the ultrashort pulsed laser light emitted from the laser light source.

When the wavelength of the ultrashort pulsed laser light emitted by the laser light source changes and the fiber switching unit is operated in response thereto to transmit the ultrashort pulsed laser light of that wavelength, an optical fiber that exhibits negative group velocity dispersion that can compensate for the positive group velocity dispersion due to the optical elements other than the optical fiber is selected. As a result, ultrashort pulsed laser light whose pulse width is compressed is irradiated onto the specimen, which allows the multiphoton-excitation effect to be efficiently generated.

The aspect of the invention described above may also include a first optical fiber imparting negative group velocity dispersion; a plurality of second optical fibers imparting different amounts of positive group velocity dispersion; and a switching unit that selects one of the second optical fibers to transmit the ultrashort pulsed laser light transmitted by the first optical fiber based on the wavelength of the ultrashort pulsed laser light emitted from the laser light source.

With this configuration, the second optical fiber is selected by operating the fiber switching unit, based on the wavelength of the ultrashort pulsed laser light emitted from the laser light source. In other words, since the amount of negative group velocity dispersion in the first optical fiber varies depending on the wavelength of the ultrashort pulsed laser light, the variation can be compensated for by selecting the second optical fiber, and the group velocity dispersion of the entire apparatus can be made substantially zero.

In this case, the second optical fibers may be formed of a plurality of optical fibers of the same type and having different lengths. Since the optical fibers are made to have different amounts of group velocity dispersion by varying their lengths, it is possible to easily realize the object of the invention described above.

According to the first aspect of the invention described above, by providing the dispersion-compensating member in the measurement head, a number of different measurement heads can be provided as individual units. In particular, it is possible to construct a measurement head having different optical systems, depending on the object to be measured. In such a case, it is possible to suitably compensate for the variation in the amount of group velocity dispersion in the measurement head due to the different optical systems by means of the dispersion-compensating member provided inside each measurement head. Therefore, an advantage is afforded in that it is possible to consistently and efficiently produce the multiphoton-excitation effect and to obtain clear fluorescence images.

Furthermore, according to the second aspect of the invention described above, it is possible to construct a simple, compact apparatus by performing compensation of the group velocity dispersion using the optical fiber. Therefore, an advantage is afforded in that it is possible to efficiently produce the multiphoton-excitation effect and to acquire detailed fluorescence images.

DETAILED DESCRIPTION OF THE INVENTION

First Embodiment

A multiphoton-excitation-type examination apparatus 1 according to a first embodiment of the present invention will be described below with reference to FIG. 1.

Figure 1:
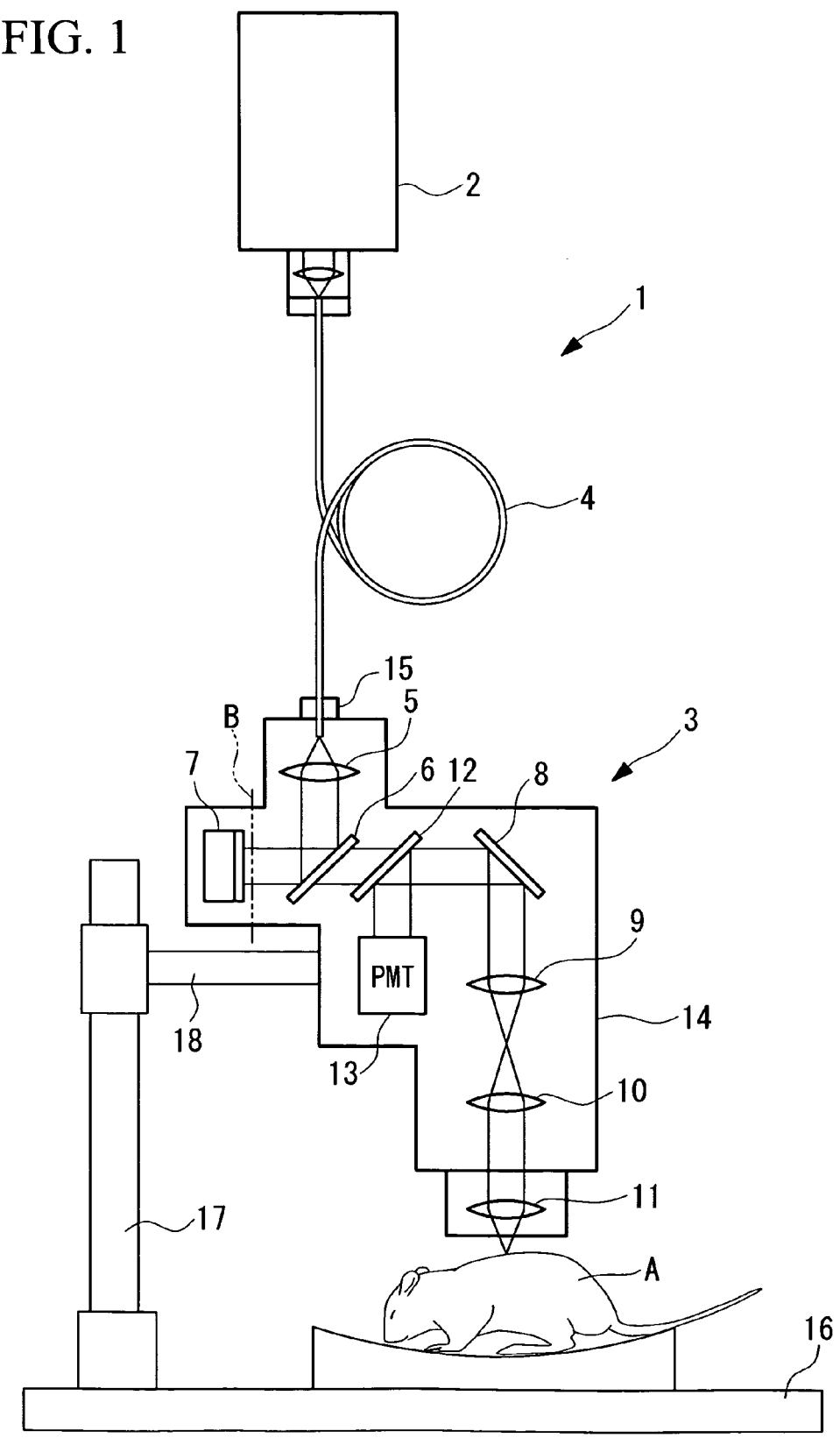
FIG. 1 is an overall structural diagram schematically showing a multiphoton-excitation-type examination apparatus according to a first embodiment of the present invention.

As shown in FIG. 1, the multiphoton-excitation-type examination apparatus 1 according to this embodiment is formed of a laser light source 2, a measurement head 3, and an optical fiber 4 that connects the laser light source 2 and the measurement head 3. The laser light source 2 is a light source that generates near-infrared ultrashort pulses of light, for example, with a pulse width of about 100 fs (femtoseconds), such as a Ti:sapphire laser light source.

The measurement head 3 includes a collimator lens 5 that collimates the ultrashort pulsed light transmitted by the optical fiber 4; a half-mirror 6 that reflects the collimated light from the collimator lens 5; a dispersion-compensating mirror (dispersion-compensating member) 7 on which the light reflected by the half-mirror 6 is incident; an optical scanning unit 8 that two-dimensionally scans light from the dispersion-compensating mirror 7; a pupil-projection optical system 9 that images the light scanned by the optical scanning unit 8 at an intermediate image position; an imaging optical system 10 and an objective optical system 11 that re-image the intermediate image formed by the pupil-projection optical system 9 onto a specimen A; a dichroic mirror 12 that splits off from the optical path fluorescence produced in the specimen A and returning via the objective optical system 11, the imaging optical system 10, the pupil-projection optical system 9, and the optical scanning unit 8; and a photomultiplier tube (PMT) 13 that detects this split-off fluorescence. All of these components are contained inside a measurement-head main body 14.

The measurement-head main body 14 is detachably connected to one end of the optical fiber 4 by means of a connector 15.

The dispersion-compensating mirror 7 is designed so that, upon reflecting the light reflected by the half-mirror 6, it imparts negative group velocity dispersion to the ultrashort pulsed laser light, which experiences positive group velocity dispersion in the optical fiber 4. The amount of negative group velocity dispersion in the dispersion-compensating mirror 7 is set so that the sum of the positive group velocity dispersion experienced in the optical fiber 4 and the positive group velocity dispersion occurring upon transmission through other optical elements in the measurement head 3 is compensated to zero.

Reference numeral 16 in the figure represents a base for mounting the specimen A, reference numeral 17 represents a support stand extending perpendicularly from the base, and reference numeral 18 represents an arm for supporting the measurement head 3 in such a manner that the measurement head 3 can be moved upwards and downwards along the support stand 17 and positioned at an angle.

The operation of the multiphoton-excitation-type examination apparatus 1 according to this embodiment, having such a configuration, will now be described below.

To carry out examination of an examination site, such as subdermal tissue or tissue below the surface of an internal organ of the specimen A, for example, a small laboratory animal, with the multiphoton-excitation-type examination apparatus 1 according to this embodiment, the laser light source 2 is operated to introduce ultrashort pulsed laser light into the optical fiber 4. The ultrashort pulsed laser light introduced into the optical fiber 4 experiences positive group velocity dispersion, which is generated inside the optical fiber 4 as the light propagates therethrough, thus lengthening the pulse width.

Then, the ultrashort pulsed laser light emitted from the end face of the optical fiber 4 is collimated by the collimator lens 5, and thereafter, the component reflected at the half-mirror 6 is reflected by the dispersion-compensating mirror 7. Since the dispersion-compensating mirror 7 is designed to compensate for the positive group velocity dispersion occurring in the optical fiber 4 and in the optical components in the measurement head 3, negative group velocity dispersion is imparted by reflection at the dispersion-compensating mirror 7. That is to say, the ultrashort pulsed laser light reflected at the dispersion-compensating mirror 7 is light having the same amount of negative group velocity dispersion as the positive group velocity dispersion imparted at the half-mirror 6, the dichroic mirror 12, the optical scanning unit 8, the pupil-projection optical system 9, the imaging optical system 10, and the objective optical system 11, through which the light passes after the dispersion-compensating mirror 7.

As a result, when it is irradiated onto the examination site from the objective optical system 11, the ultrashort pulsed laser light has a pulse width of about 100 fs, which is equal to that emitted from the laser light source 2. Therefore, it is possible to easily generate the multiphoton excitation effect at the examination site.

Then, fluorescence produced by the multiphoton-excitation effect at the examination site passes through the objective optical system 11, the imaging optical system 10, the pupil-projection optical system 9, the optical scanning unit 8, and the dichroic mirror 12, is incident on the photomultiplier tube 13, and is acquired as a detailed fluorescence image.

In this case, with the multiphoton-excitation-type examination apparatus 1 according to this embodiment, since the dispersion-compensating member is formed of the dispersion-compensating mirror 7, the positive group velocity dispersion can be compensated for simply by reflecting the ultrashort pulsed laser light. Therefore, the structure can be simplified by using fewer parts, and it is possible to make the measurement-head main body 14, which includes the dispersion-compensating mirror 7, more compact.

Also, the amount of dispersion compensation of the dispersion-compensating mirror 7 is set so as to achieve compensation of the group velocity dispersion in the various optical elements contained in the measurement-head main body 14, in addition to the group velocity dispersion in the optical fiber 4. Therefore, when changing the optical elements to match the site being examined, the group velocity dispersion of the ultrashort pulsed laser light can be compensated for simply by detaching the measurement head 3 from the optical fiber 4 with the connector 15 and replacing it with a measurement head 3 having a different optical system. This allows ultrashort pulsed laser light with a short pulse width to be emitted from the objective optical system 11.

In other words, by providing the replaceable measurement head 3 with a dispersion-compensating mirror 7 that compensates for the group velocity dispersion in the entire multiphoton-excitation-type examination apparatus 1, it is possible to automatically compensate for the group velocity dispersion by changing the measurement head 3, without changing the laser light source 2 and the optical fiber 4.

The dispersion-compensating mirror 7 can compensate for the group velocity dispersion even when the group velocity dispersion changes when changing the laser wavelength.

Also, in the embodiment described above, a description has been given of the case where the ultrashort pulsed laser light emitted from the laser light source 2 is directly introduced into the optical fiber 4; however, since the ultrashort pulsed laser light has an extremely short pulse width, the peak power thereof is high. The optical fiber 4 has a characteristic whereby if the power of the laser light introduced into the optical fiber 4 is high, a correspondingly high nonlinear effect is produced.

Figure 2:
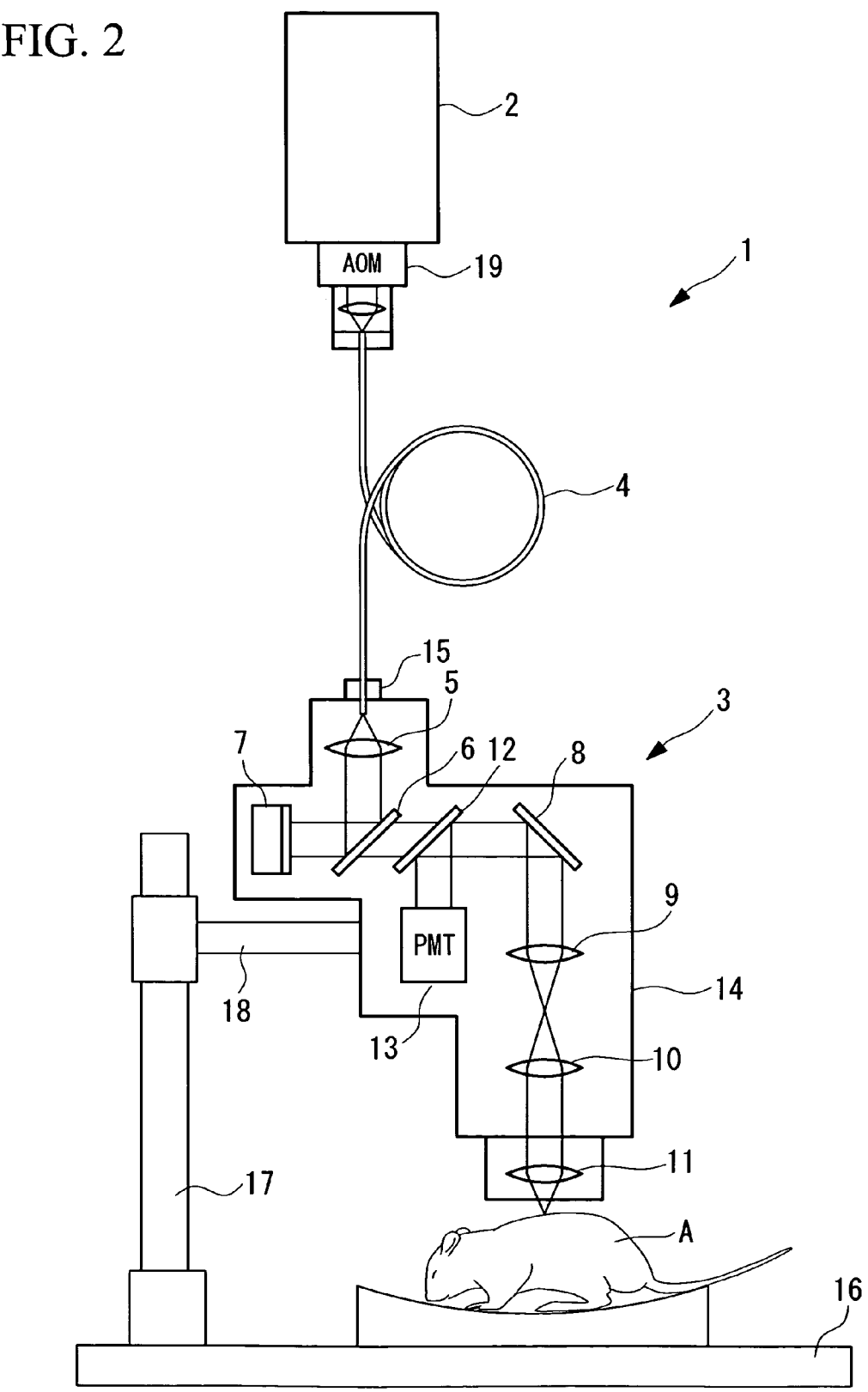
FIG. 2 is an overall structural diagram showing a modification of the multiphoton-excitation-type examination apparatus in FIG. 1.

Therefore, as shown in FIG. 2, a dispersion-imparting member 19 that imparts positive group velocity dispersion to the ultrashort pulsed laser light, for example, an acousto-optic modulator (AOM), may be provided between the laser light source 2 and the optical fiber 4. By doing so, positive group velocity dispersion smaller than that in the case of the first embodiment described above can be imparted to the ultrashort pulsed laser light entering the measurement head from the optical fiber 4. Therefore, by setting the amount of dispersion compensation imparted by the dispersion-compensating mirror 7 in the measurement head 3 to be smaller by the same amount, it is possible to achieve the same advantages as described above.

With this configuration, since it is possible to set the pulse width of the ultrashort pulsed laser light to be longer when passing through the optical fiber 4, there is also an advantage in that it is possible to maintain the integrity of the optical fiber 4.

In this embodiment, a description has been given of a case in which the dispersion-compensating mirror 7 is fixed inside the measurement head 3. However, the invention is not limited to this configuration; the dispersion-compensating mirror 7 may be provided at the position indicated by the broken line B in FIG. 1 so that it can be detached from the measurement-head main body 14 and replaced with another one. With this configuration, suitable dispersion compensation can be carried out even when optical elements other than the measurement head 3 change.

In addition, since the optical fiber 4 is removable by means of the connector 15, servicing and replacement when the optical fiber 4 becomes damaged are facilitated. Also, in order that the optical fiber 4 may not be removed when a user is operating the apparatus, the connector 15 may be attached by bonding, or a locking mechanism for mechanically preventing its removal may be provided.

Second Embodiment

Figure 3:
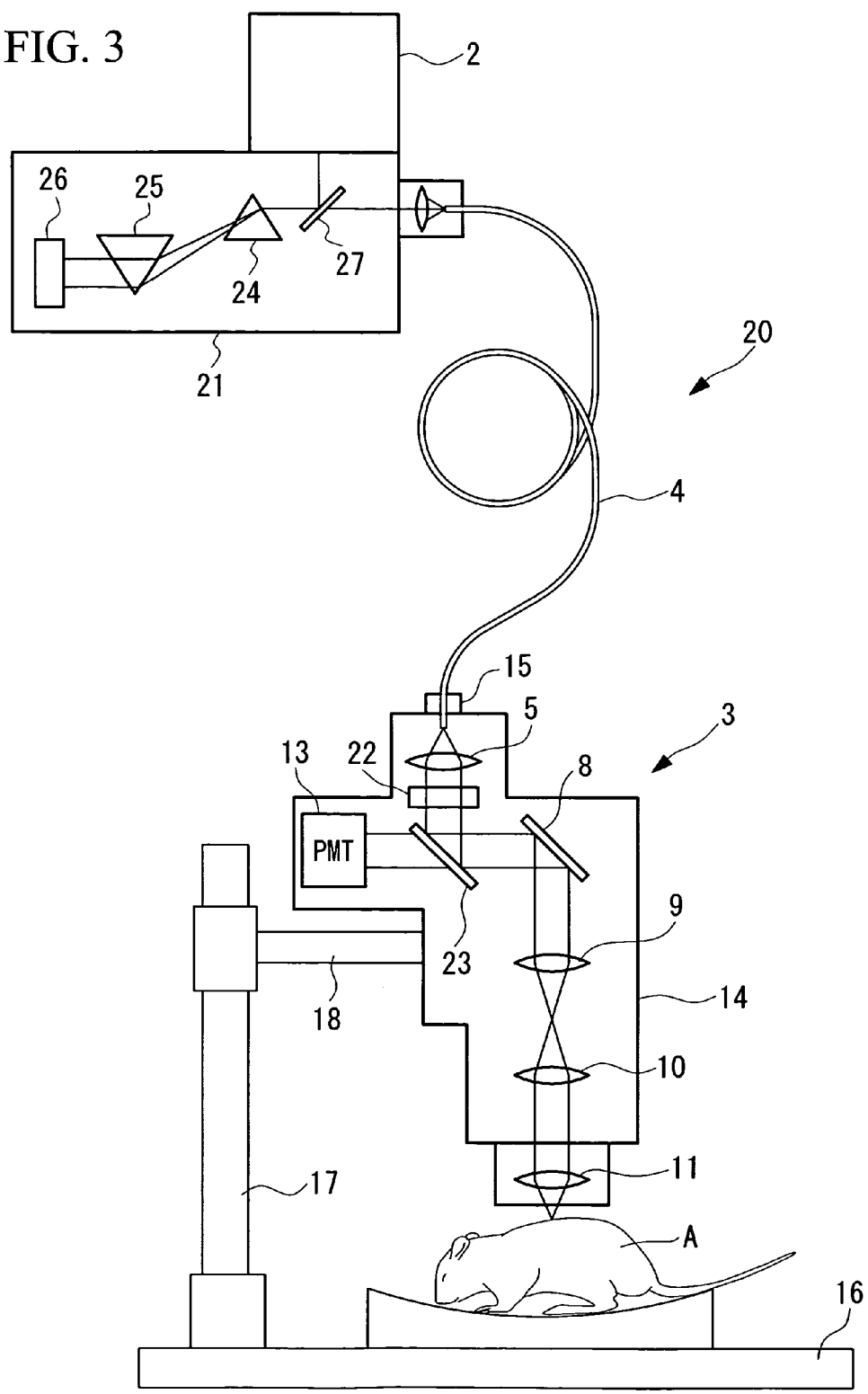
FIG. 3 is an overall structural diagram schematically showing a multiphoton-excitation-type examination apparatus according to a second embodiment of the present invention.

Next, a multiphoton-excitation-type examination apparatus 20 according to a second embodiment of the present invention will be described below with reference to FIG. 3.

Parts in the description of this embodiment having the same configuration as those in the multiphoton-excitation-type examination apparatus 1 according to the first embodiment described above are assigned the same reference numerals, and a description thereof is omitted here.

The multiphoton-excitation-type examination apparatus 20 according to this embodiment differs from the multiphoton-excitation-type examination apparatus 1 according to the first embodiment in that a first dispersion-imparting member 21 is provided between the laser light source 2 and the optical fiber 4, and a dispersion-imparting member provided inside the measurement head 3 is a second dispersion-imparting member 22 for imparting positive group velocity dispersion. Reference numeral 23 represents a dichroic mirror that is designed, on one hand, to reflect light passing through the second dispersion-imparting member 22 to the optical scanning unit 8 side and, on the other hand, to transmit fluorescence returning from the optical scanning unit 8 and direct it towards the photomultiplier tube 13.

The first dispersion-imparting member 21 is, for example, a pre-chirper formed of two prisms 24 and 25 and a mirror 26. By keeping the distance between the two prisms 24 and 25 large, the transmission lengths of long wavelength light and short wavelength light through the prisms 24 and 25 differ, and as a result, negative group velocity dispersion is applied to the ultrashort pulsed laser light entering the optical fiber 4. Thus, by applying the negative group velocity dispersion in this way, it is possible to sufficiently lengthen the pulse width of the ultrashort pulsed laser light introduced into the optical fiber 4. This allows the generation of nonlinear effects in the optical fiber to be suppressed, and the integrity of the optical fiber 4 can thus be maintained. Reference numeral 27 in the figure is a mirror. The mirror 27 reflects light from the light source 2 towards the prism 24. After passing through the prism 25, the light reflected at the mirror 26 bypasses the mirror 27 and is introduced into the optical fiber 4.

On the other hand, the second dispersion-imparting member 22, which is made, for example, of zinc selenide (ZnSe) or tellurium oxide ($TeO_2$) crystal, is designed to impart positive group velocity dispersion by transmitting the ultrashort pulsed laser light collimated by the collimator lens 5. This second dispersion-imparting member 22 compensates for the group velocity dispersion in the entire multiphoton-excitation-type examination apparatus 20, like the dispersion-compensating mirror 7 in the first embodiment described above. That is, since a large negative group velocity dispersion is imparted in the first dispersion-imparting member 21 and a positive group velocity dispersion smaller than this is imparted by the optical fiber 4 and the other optical elements in the measurement head 3, the second dispersion-imparting member 22 imparts positive group velocity dispersion to compensate for this.

With multiphoton-excitation-type examination apparatus 20 according to this embodiment, having such a configuration, it is possible to realize a compact measurement head 3, as with the multiphoton-excitation-type examination apparatus 1 according to the first embodiment. In addition, the multiphoton-excitation effect can be efficiently generated by compensating for the group velocity dispersion. Also, providing the dispersion-imparting member 22 in the measurement head 3 allows the group velocity dispersion to be compensated for even when replacing the measurement head 3 with another one having a different optical system, without changing the laser light source 2 and the optical fiber 4. Furthermore, by disposing the dispersion-imparting member 22 before the optical scanning unit 8, it is possible to prevent changes in the amount of dispersion compensation due to changing of the optical axis direction by the scanning, thus realizing reliable dispersion compensation.

Figure 4:
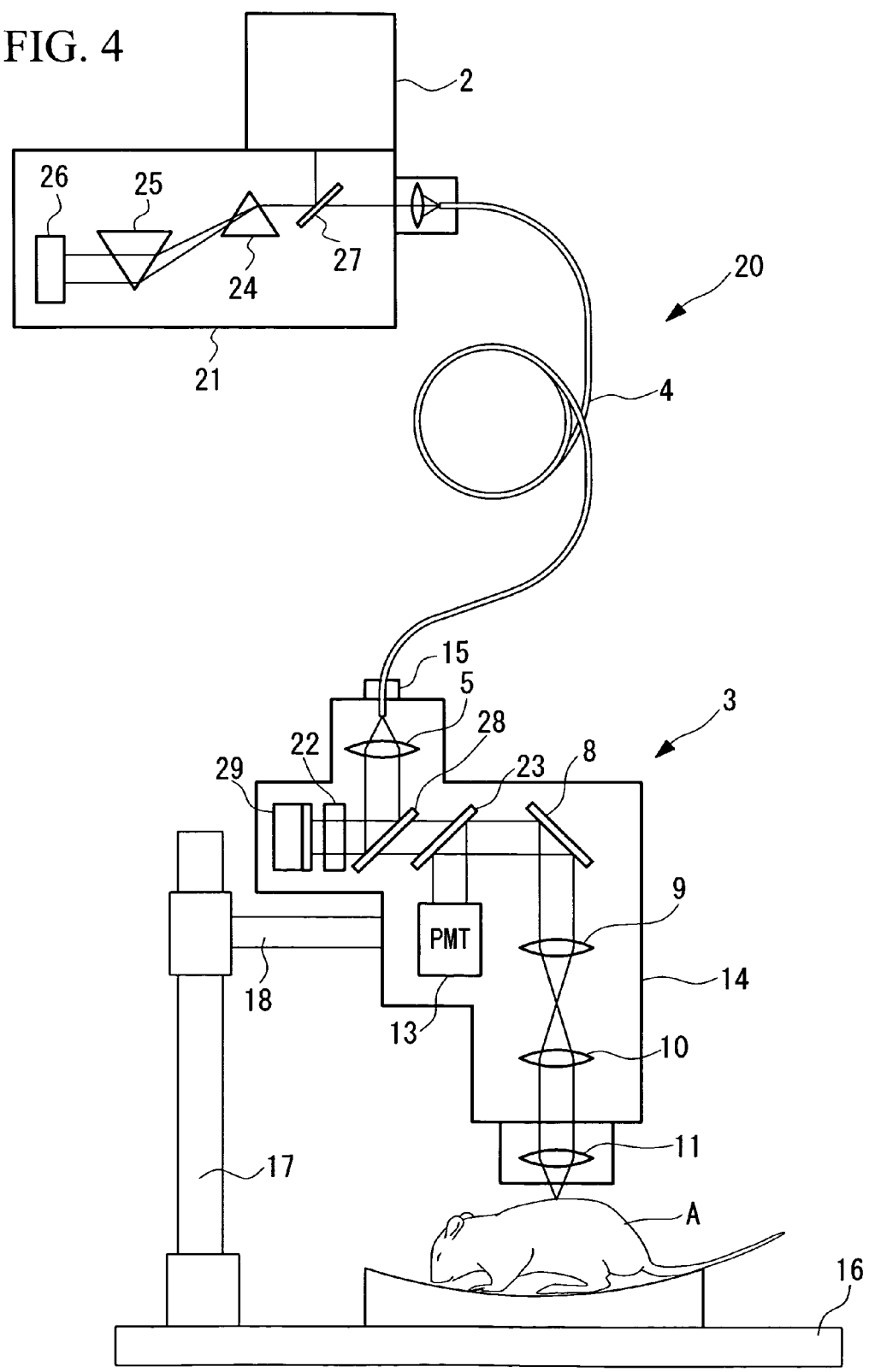
FIG. 4 is an overall structural diagram showing a modification of the multiphoton-excitation-type examination apparatus in FIG. 3.

In the second embodiment described above, the light passing through the collimator lens 5 is transmitted through the second dispersion-imparting member 22 and is directed towards the optical scanning unit 8 by the dichroic mirror 23. Instead of this, however, as shown in FIG. 4, it is also possible that the light passing through the collimator lens 5 is guided in the direction opposite to the optical scanning unit 8 by a half-mirror 28 to be transmitted through the dispersion-imparting member 22 and then transmitted again through the dispersion-imparting member 22 after being reflected at a mirror 29. Thereafter, the light passing through the half-mirror 28 is guided towards the optical scanning unit 8. With this arrangement, since the light is transmitted twice through the same dispersion-imparting member 22, the amount of dispersion compensation imparted each time need only be half, and the thickness can thus be reduced by half.

Third Embodiment

Next, a multiphoton-excitation-type examination apparatus 30 according to a third embodiment of the present invention will be described below with reference to FIGS. 5 and 6.

Parts in the description of this embodiment having the same configuration as in the multiphoton-excitation-type examination apparatus 20 according to the second embodiment described above are assigned the same reference numerals, and a description thereof shall be omitted here.

The multiphoton-excitation-type examination apparatus 30 according to this embodiment differs from the multiphoton-excitation-type examination apparatus 20 according to the second embodiment in that a second dispersion-imparting member 31 serving as the dispersion-compensating member produces positive group velocity dispersion, and an adjusting mechanism 32 is provided for adjusting the group velocity dispersion thereof.

Figure 5:
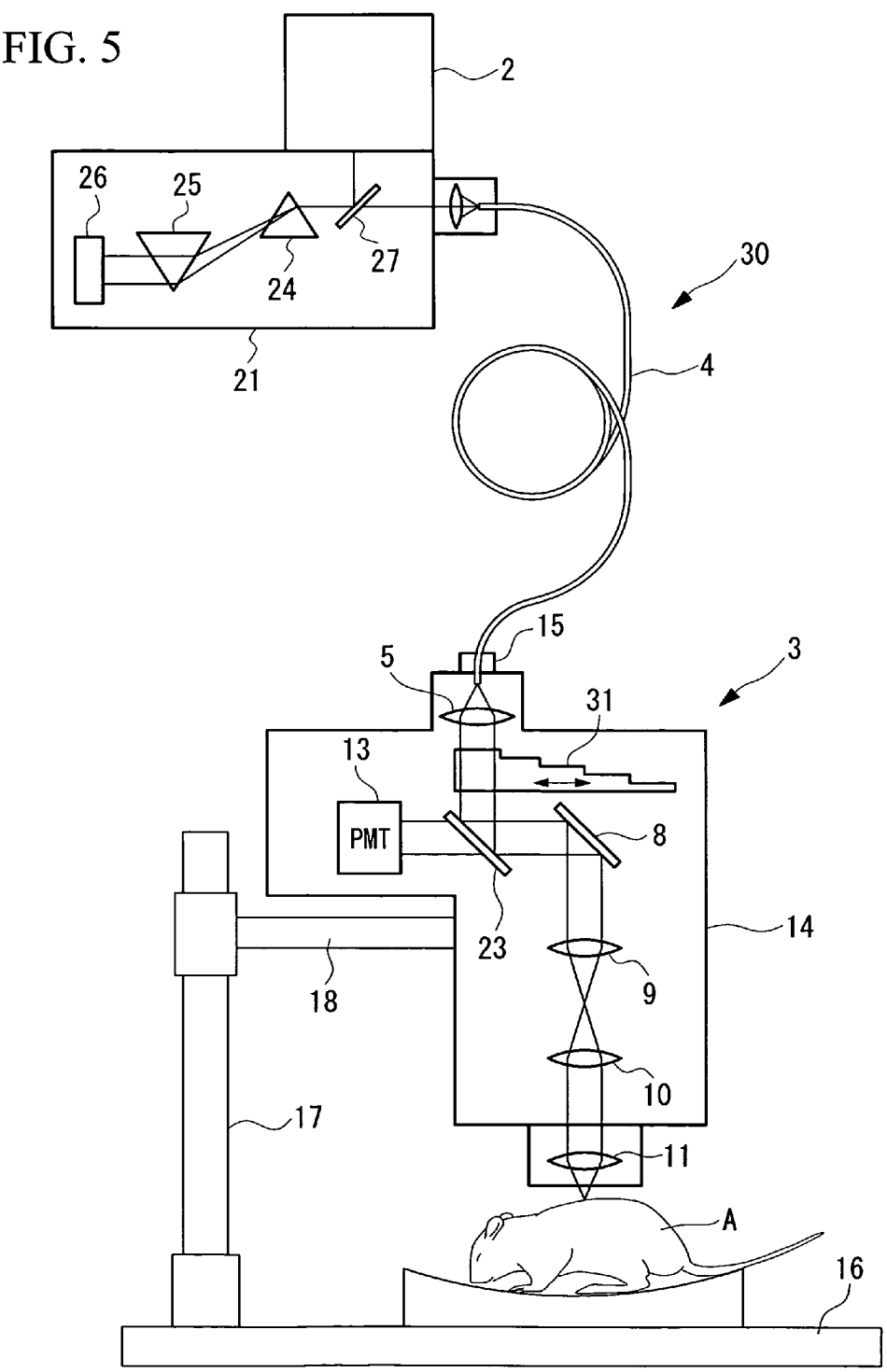
FIG. 5 is an overall structural diagram schematically showing a multiphoton-excitation-type examination apparatus according to a third embodiment of the present invention.
Figure 6:
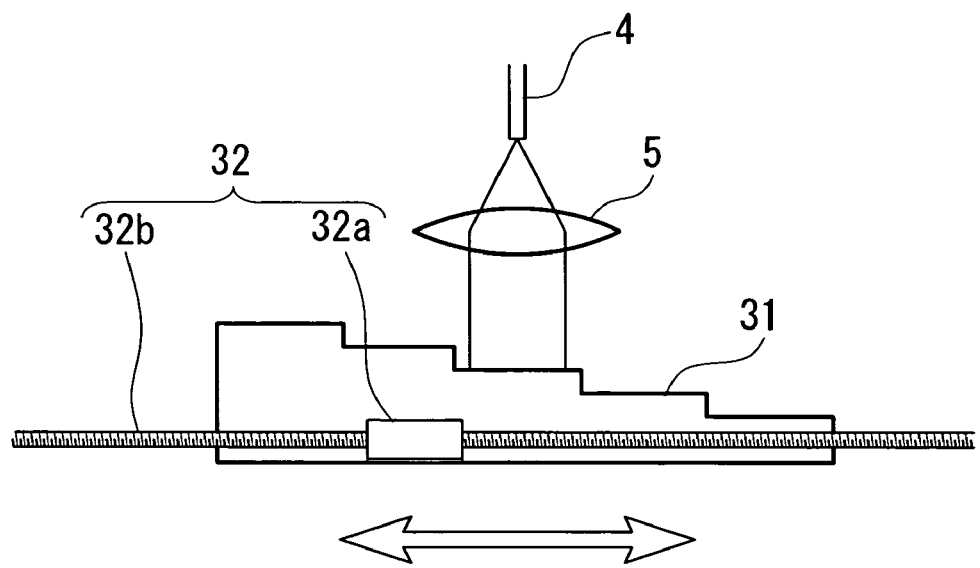
FIG. 6 is front elevation showing a dispersion-compensating member and an adjustment mechanism in the multiphoton-excitation-type examination apparatus in FIG. 5.

For example, as shown in FIG. 5 and FIG. 6, a member that can select different amounts of dispersion compensation may be used as the second dispersion-imparting member 31. This is achieved by forming the member of zinc selenide (ZnSe) or tellurium oxide (TeO$_2$) crystal in a stepped structure having a plurality of thicknesses and making the ultrashort pulsed laser light pass through at different positions.

As shown in FIG. 6, for example, the adjusting mechanism 32 includes a nut 32a attached to the side face of the second dispersion-imparting member 31, in which a plurality of parts having different thicknesses are arranged in a direction orthogonal to the optical axis, and a lead screw 32b that moves the nut 32a in a direction orthogonal to the optical axes. By rotatably attaching the lead screw 32b to, for example, the measurement-head main body 14 and rotating it about the axis thereof, either manually or with a motor or the like, it is possible to move the nut 32a and the second dispersion-imparting member 31 in a direction orthogonal to the optical axis.

With the multiphoton-excitation-type examination apparatus 30 according to this embodiment, having such a configuration, if the group velocity dispersion of the entire apparatus changes when the objective optical system 11 is replaced with another one of a different type, the optical fiber 4 is replaced with another one of a different type, the laser light source 2 is replaced with another one of a different type, or the wavelength of the ultrashort pulsed laser light emitted by the laser light source is changed, etc., it is possible to irradiate the specimen A with ultrashort pulsed laser light having a short pulse width by operating the adjustment mechanism 32 to change the amount of dispersion compensation of the second dispersion-imparting member 31.

Figure 7:
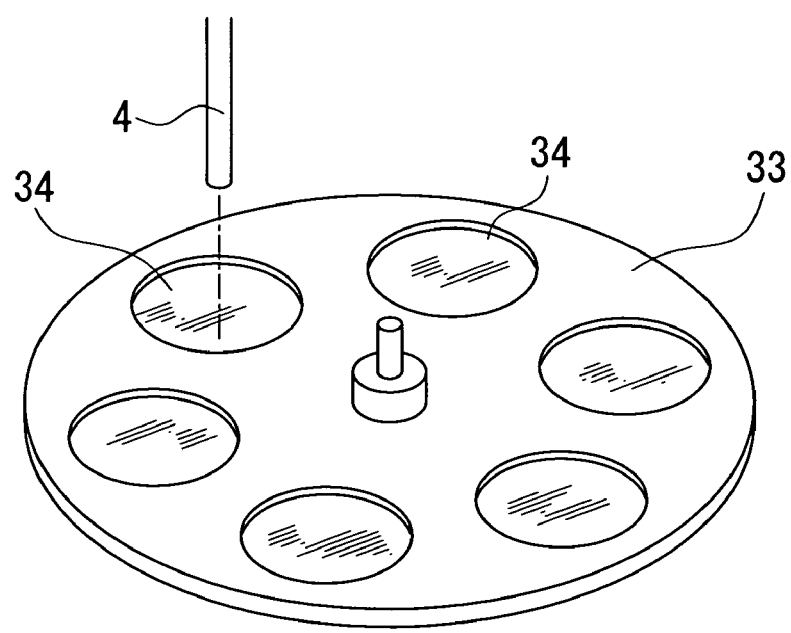
FIG. 7 is a perspective view showing a modification of the dispersion-compensating member and the adjustment mechanism in FIG. 6.
Figure 8:
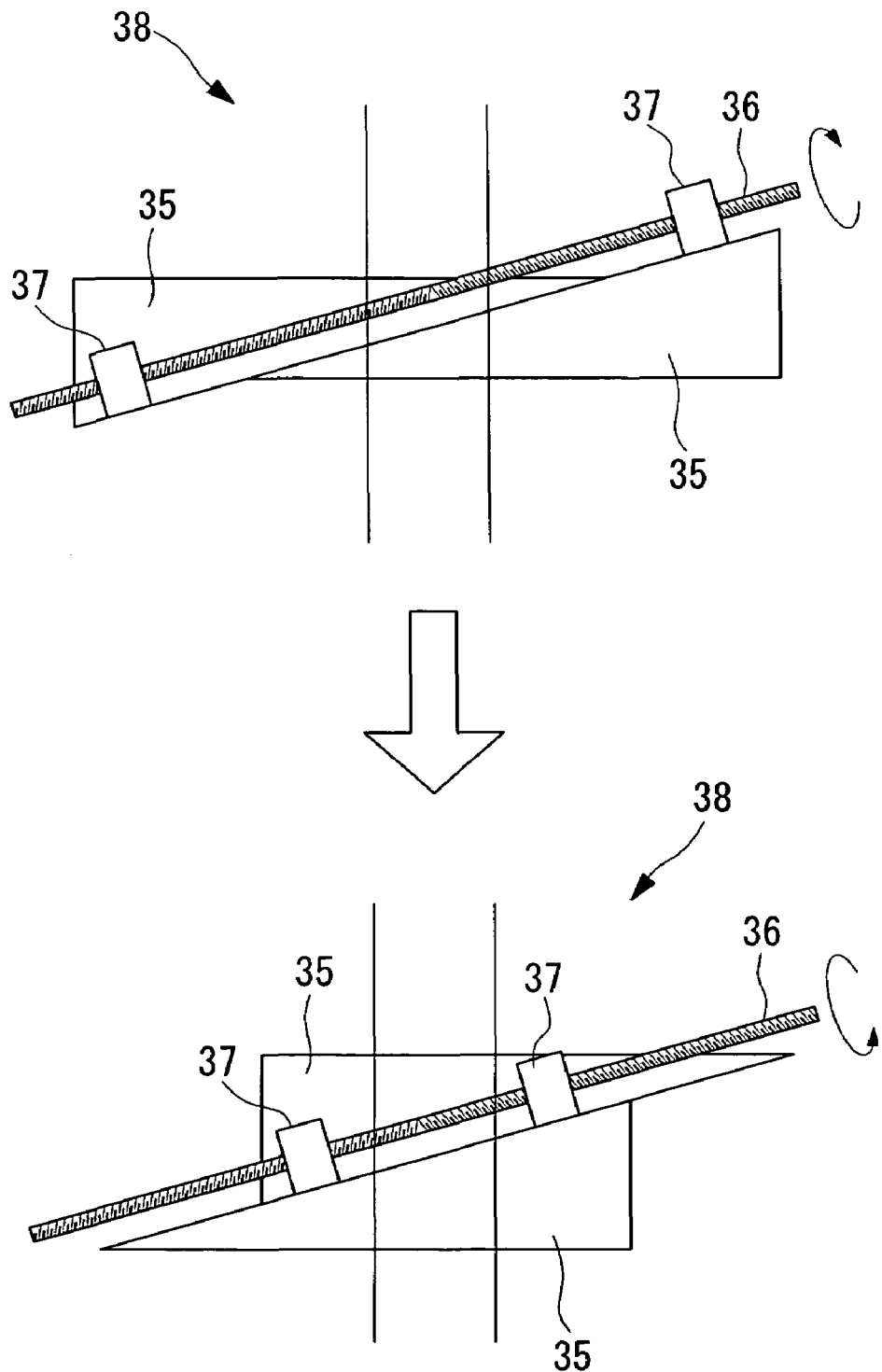
FIG. 8 is an explanatory diagram showing another modification of the dispersion-compensating member and the adjustment mechanism in FIG. 6.

In addition to the structure shown in FIG. 6, a mechanism having any structure can be used as the adjustment mechanism 32. As shown in FIG. 7, as the procedure for adjusting the amount of dispersion compensation, the amount of group velocity dispersion may be selected by disposing a plurality of dispersion-compensating members 34 that produce different amounts of group velocity dispersion around the circumference of a rotating plate 33 and rotating the rotating plate 33 as required. Also, as shown in FIG. 8, a second dispersion-imparting member 38 may be configured by combining two wedge-shaped dispersion-compensating plates 35 in close contact, for example, by engaging a lead screw 36 that is threaded at both ends with nuts 37 that are fixed to the dispersion-compensating plates 35, respectively, and disposed parallel to the contact faces. With this configuration, when the lead screw 36 is rotated, the two dispersion-compensating plates 35 move relative to each other while remaining in contact, and as a result, the thickness dimension parallel to the optical axis can be varied gradually. Therefore, the amount of dispersion compensation can be gradually varied to set it at a desired value.

The dispersion-imparting member 31 having such an adjustment mechanism 32 may be provided in the measurement head 3; however, if it cannot be made compact, it may be disposed between the laser light source 2 and the optical fiber 4. The amount of dispersion compensation can also be adjusted by changing the distance between the prisms 24 and 25 in the pre-chirper in the second embodiment; in this case, however, there is a drawback in that the optical axis becomes shifted, whereas in the present embodiment, it is possible to adjust the amount of dispersion compensation by using the adjustment mechanism 32 without moving the optical axis.

Fourth Embodiment

Next, a multiphoton-excitation-type examination apparatus 40 according to a fourth embodiment of the present invention is described below with reference to FIGS. 9 and 10.

Parts in the description of this embodiment having the same configuration as those in the multiphoton-excitation-type examination apparatus 1 according to the first embodiment described above are assigned the same reference numerals, and a description thereof is omitted here.

The difference between the multiphoton-excitation-type examination apparatus 40 according to this embodiment and the multiphoton-excitation-type examination apparatus 1 according to the first embodiment lies in an objective optical system 41.

In this embodiment, a dispersion-compensating unit 43 is provided in an objective unit 42 that houses the objective optical system 41.

Figure 9:
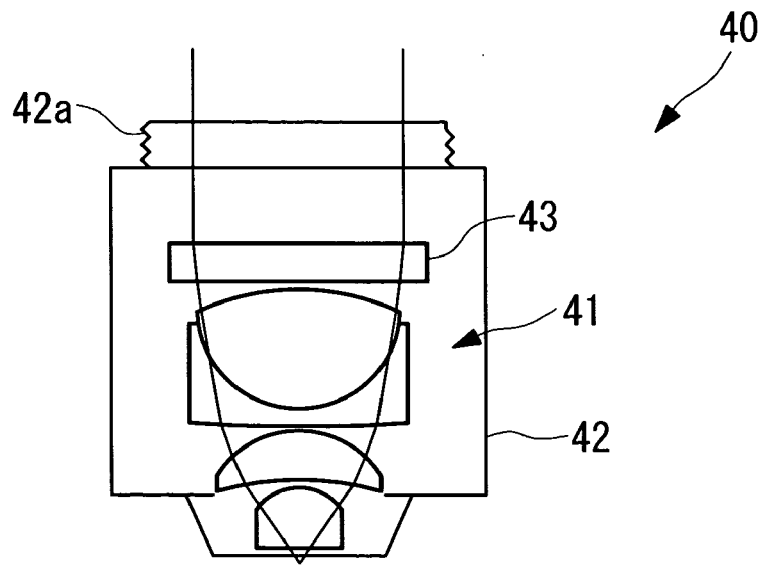
FIG. 9 is a cross-section schematically showing an objective unit of a multiphoton-excitation-type examination apparatus according to a fourth embodiment of the present invention.

As shown in FIG. 9, for example, the dispersion-compensating unit 43 is provided in the objective unit 42, which is detachably connected to the measurement head 3, and is designed so that the amount of group velocity dispersion in the entire objective unit 42 is constant. A screw 42a is provided in the objective unit 42 for detachably connecting it to the measurement head 3.

In the example shown in FIG. 9, a transmission-type dispersion-compensating member (dispersion-compensating unit) 43 that transmits ultrashort pulsed laser light towards the lenses constituting the objective optical system is inserted at the incident side, and the group velocity dispersion produced by the objective optical system 41 is set at a predetermined value.

Figure 10:
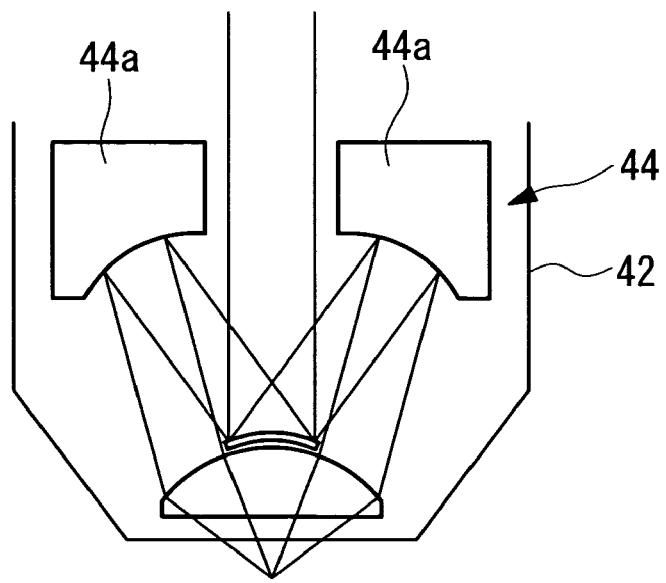
FIG. 10 is a cross-section schematically showing a modification of the objective unit in FIG. 9.

In the example shown in FIG. 10, reflective-type objective lenses 44a that do not transmit ultrashort pulsed laser light are used in part of or the entirety of an objective optical system 44. With this configuration, it is possible to reduce the group velocity dispersion while maintaining the required magnification, transmittance, and numerical aperture, which allows the amount of group velocity dispersion to be reduced compared to the case where standard transmissive lenses are used.

A reflective-type dispersion-compensating unit like the dispersion-compensating mirror 7 disclosed in the first embodiment may be used, if permitted by space considerations.

With the multiphoton-excitation-type examination apparatus 40 according to this embodiment, having such a configuration, the overall group velocity dispersion does not change, even if the objective unit 42 is changed, and it is thus possible to consistently and efficiently generate the multiphoton-excitation effect and to obtain detailed fluorescence images.

In the embodiments described above, compensation of the group velocity dispersion in the measurement head 3 has been described; instead of this, however, in addition to the dispersion-compensating member in the measurement head 3, the overall group velocity dispersion may be compensated for by using an optical fiber 4 that imparts negative group velocity dispersion, such as a photonic crystal fiber, for example.

Fifth Embodiment

Next, a multiphoton-excitation-type examination apparatus 101 according to a fifth embodiment of the present invention will be described with reference to FIG. 11.

Figure 11:
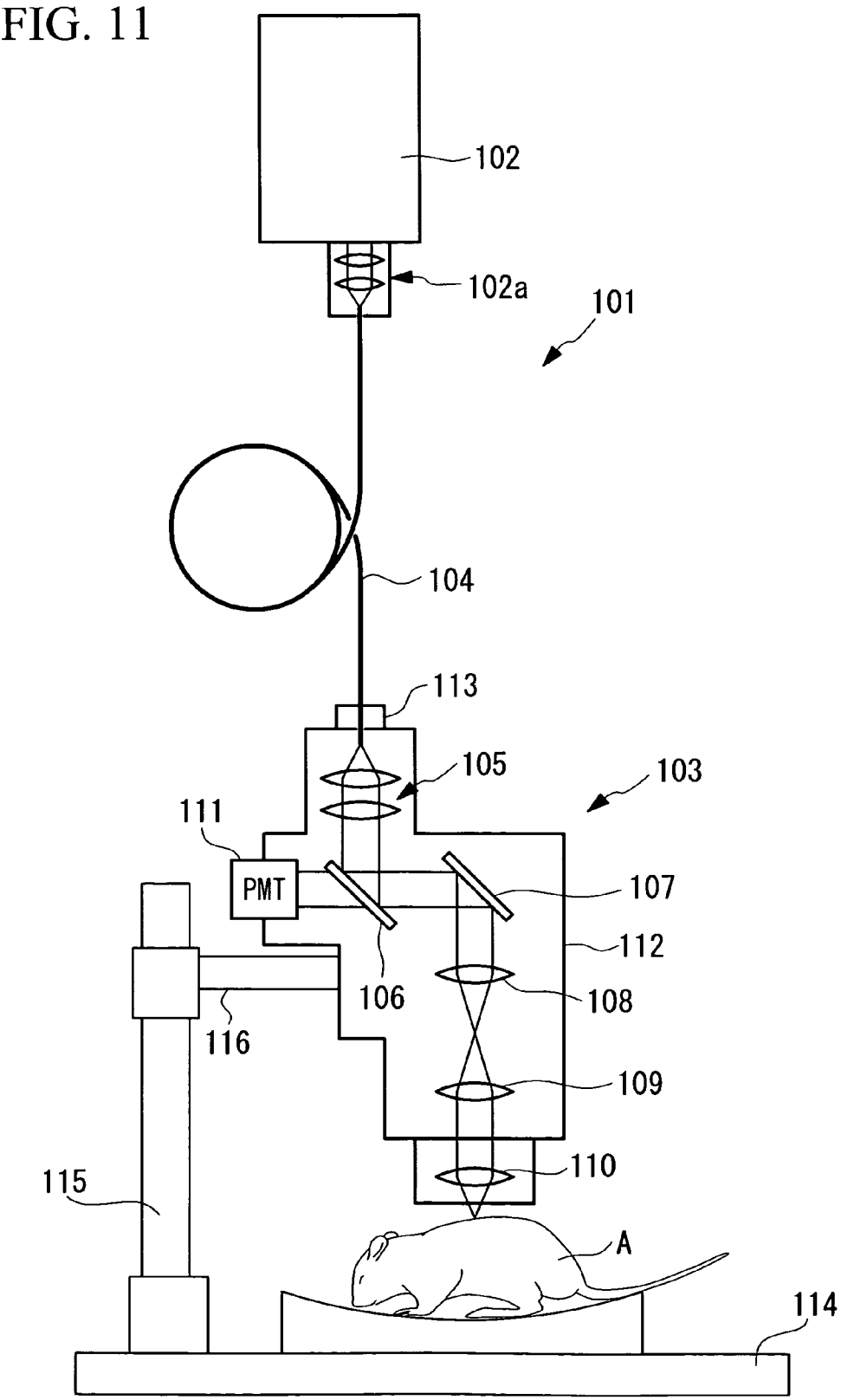
FIG. 11 is an overall structural diagram schematically showing a multiphoton-excitation-type examination apparatus according to a fifth embodiment of the present invention.

As shown in FIG. 11, the multiphoton-excitation-type examination apparatus 101 of this embodiment is formed of a laser light source 102, a measurement head 103, and an optical fiber 104 that connects the laser light source 102 and the measurement head 103. The laser light source 102 emits near-infrared ultrashort pulsed laser light having a pulse width of, for example, 100 fs (femtoseconds), such as a Ti:sapphire laser light source.

The measurement head 103 includes a collimator lens 5 that collimates the ultrashort pulsed laser light transmitted by the optical fiber 104; a dichroic mirror 106 that reflects the collimated light from the collimator lens 105; an optical scanning unit 107 that two-dimensionally scans the light reflected by the dichroic mirror 106; a pupil-projection optical system 108 that images the light scanned by the optical scanning unit 107 at an intermediate image position; an imaging optical system 109 and an objective optical system 110 that re-image the intermediate image formed by the pupil-projection optical system 108 onto a specimen A; and a photomultiplier tube (PMT) 111 that detects fluorescence produced in the specimen A and returning via the objective optical system 110, the imaging optical system 109, the pupil-projection optical system 108, the optical scanning unit 107, and the dichroic mirror 106. All of these components are contained inside a measurement-head main body 112. Reference numeral 114 in the figure represents a base for mounting the specimen A, reference numeral 115 represents a support stand extending perpendicularly from the base 114, and reference numeral 116 represents an arm that moves the measurement head 103 upwards and downwards along the support stand 115 and can supports it an angle.

The measurement head 112 is detachably connected to one end of the optical fiber 104 via a connector 113.

A fiber that exhibits zero group velocity dispersion when the ultrashort pulsed laser light propagating inside has a predetermined wavelength and that produces group velocity dispersions with different signs depending on whether the wavelength is longer or shorter than this wavelength is used as the optical fiber 104. Such a fiber is, for example, a photonic crystal fiber.

A photonic crystal fiber that makes the group velocity dispersion at wavelengths different from the wavelength of the propagating ultrashort pulsed laser light zero is selected as the optical fiber 104 used here, and thus the optical fiber 104 itself exhibits negative group velocity dispersion. The amount of negative group velocity dispersion exhibited by the optical fiber 104 is set to be the same as the amount of positive group velocity dispersion due to the other optical elements, for example, collimator lenses 102a disposed at the exit window of the laser light source 102 or the various optical systems 105, 108, 109, and 110 in the measurement head 103.

The operation of the multiphoton-excitation-type examination apparatus 101 according to this embodiment, having such a configuration, will be described below.

To carry out examination of an examination site, such as subdermal tissue or tissue below the surface of an internal organ of the specimen A, for example, a small laboratory animal, using the multiphoton-excitation-type examination apparatus 101 according to this embodiment, the laser light source 102 is operated and ultrashort pulsed laser light is transmitted to the measurement head 103 via the optical fiber 104.

The ultrashort pulsed laser light emitted to the inside of the measurement head 103 from the end of the optical fiber 104 is reflected at the dichroic mirror 106 after being collimated by the collimator lens 105, and is then incident on the optical scanning unit 107. Then, the ultrashort pulsed laser light reflected at the optical scanning unit 107 is re-imaged onto the specimen A via the pupil-projection optical system 108, the imaging optical system 109, and the objective optical system 110, and produces the multiphoton-excitation effect in the specimen A. The fluorescence produced as a result returns along the same optical path via the objective optical system 110, the imaging optical system 109, the pupil-projection optical system 108, and the optical scanning unit 107, is transmitted through the dichroic mirror 106 without being reflected thereat, and is detected by the photomultiplier tube 111. By operating the optical scanning unit 107, the position at which the light is re-imaged on the specimen A is two-dimensionally scanned, which allows two-dimensional images to be detected by the photomultiplier tube 111.

In this case, by making the light pass through the individual lenses in the optical elements included in the laser light source 102, such as the collimator lenses 102a, and in the optical systems contained in the measurement head 103, namely, the collimator lens 105, the pupil-projection optical system 108, the imaging optical system 109, and the objective optical system 110, a positive group velocity dispersion is produced by nonlinear effects due to wavelength-dependent refractive index variations in those media, which causes a corresponding lengthening of the pulse width. Accordingly, in the multiphoton-excitation-type examination apparatus 101 according to this embodiment, since the optical fiber 104 is designed to exhibit negative group velocity dispersion, the positive group velocity dispersion of the entire apparatus can be compensated for by the negative group velocity dispersion of the optical fiber 104.

As a result, the ultrashort pulsed laser light irradiating the examination site in the specimen A from the objective optical system 110 has a pulse width equal to that emitted from the laser light source 102, namely, about 100 fs, which allows the multiphoton-excitation effect to be efficiently generated at the examination site.

In this case, with the multiphoton-excitation-type examination apparatus 101 according to this embodiment, since it is possible to compensate for the group velocity dispersion of the entire apparatus using the optical fiber 104, which connects the laser light source 102 and the measurement head 103, a specially designed device is not necessary. Also, since it is not necessary to employ a pre-chirper, which is relatively large and complex, an advantage is afforded in that it is possible to construct a simple apparatus with a compact configuration.

Sixth Embodiment

Next, a multiphoton-excitation-type examination apparatus 120 according to a sixth embodiment of the present invention will be described with reference to FIG. 12.

Parts in the description of this embodiment having the same configuration as those in the multiphoton-excitation-type examination apparatus 101 according to the fifth embodiment described above are assigned the same reference numerals, and a description thereof shall be omitted here.

The difference between the multiphoton-excitation-type examination apparatus 120 according to this embodiment and the multiphoton-excitation-type examination apparatus 101 according to the fifth embodiment lies in a laser light source 121 and an optical fiber unit 122.

The laser light source 121 can switch, in a discrete, step-like manner, the wavelength of the emitted ultrashort pulsed laser light within a wavelength range of, for example, 800 to 880 nm. This switching is performed, for example, in n discrete steps.

Figure 12:
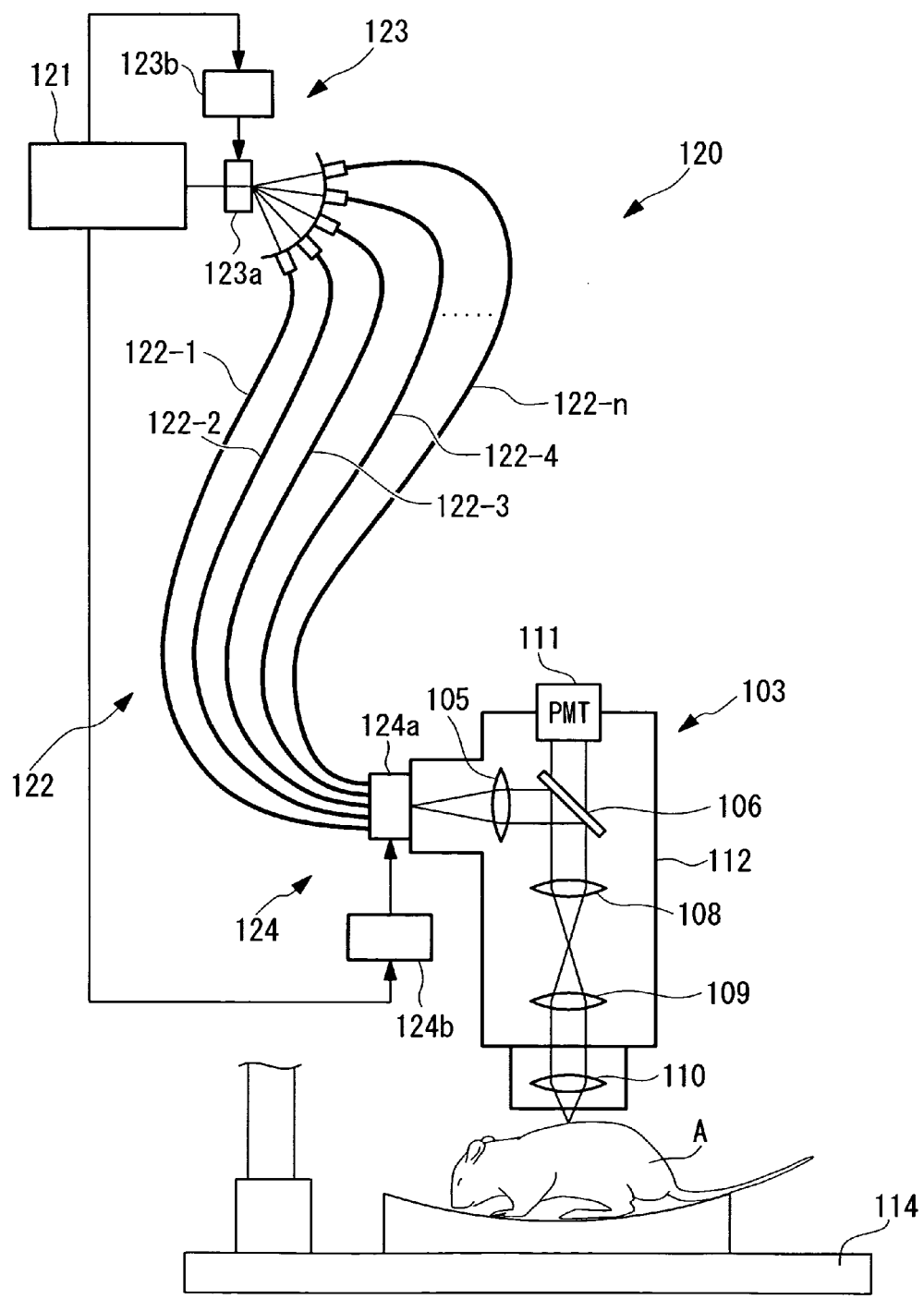
FIG. 12 is an overall structural diagram schematically showing a multiphoton-excitation-type examination apparatus according to a sixth embodiment of the present invention.

As shown in FIG. 12, the optical fiber unit 122 includes a plurality of optical fibers, for example, n optical fibers 122-1 to 122-n, and optical switches 123 and 124 provided at both ends of these optical fibers 122-1 to 122-n.

The optical fibers 122-1 to 122-n are provided to correspond to the individual wavelengths of the ultrashort pulsed laser light emitted in the step-like manner from the laser light source 121. When the ultrashort pulsed laser beams with the respective wavelengths are transmitted, the levels of negative group velocity dispersion experienced by the ultrashort pulsed laser beams are set to be identical. For example, when ultrashort pulsed laser light having a wavelength of 800 nm is emitted from the laser light source 121, the optical fiber 122-1 is selected, and when ultrashort pulsed laser light having a wavelength of 880 nm is emitted from the laser light source 121, the optical fiber 122-n is selected. When the ultrashort pulsed laser beams having the wavelengths from 800 nm to 880 nm are transmitted in the respective optical fibers 122-1 to 122-n, the same levels of negative group velocity dispersion are produced. Also, the amount of this negative group velocity dispersion is set in proportion to the amount of positive group velocity dispersion applied by optical elements other than the optical fibers 122-1 to 122-2, so that the total amount of dispersion becomes substantially zero.

The optical switches 123 and 124 may be, for example, devices that are configured to adjust the angle of galvano mirrors 123a and 124a so that the ultrashort pulsed laser beams having different wavelengths enter different optical fibers 122-1 to 122-n in response to command signals from control devices 123b and 124b, such as control devices that control the galvano mirrors 123a and 124a and the switches 123 and 124. Alternatively, a device arranged to emit the ultrashort pulsed light beams from the laser light source 121 in different directions according to the wavelength may be used, such as an acousto-optic deflector (AOD) and a control device therefor.

With the multiphoton-excitation-type examination apparatus 120 according to this embodiment, having such a configuration, when ultrashort pulsed laser beams having different wavelengths are emitted from the laser light source 121, information about those wavelengths is transmitted to the control devices 123b and 124b, and the control devices 123b and 124b indicate to the optical switches 123 and 124 which of the optical fibers 122-1 to 122-n is to be selected. Accordingly, the ultrashort pulsed laser beams emitted from the laser light source 121 are transmitted through the optical fibers 122-1 to 122-n selected in response to the wavelength, and the light is introduced into the measurement head 103.

Although the ultrashort pulsed laser beams having different wavelengths are introduced into the respective optical fibers 122-1 to 122-n, the amount of negative group velocity dispersion produced in all of the optical fibers 122-1 to 122-n is set to be identical. Therefore, the group velocity dispersion can always be compensated for and the multiphoton-excitation effect can be efficiently generated even when the examination site in the specimen A is irradiated with ultrashort pulsed laser beams having different wavelengths.

In the embodiment described above, a description has been given of an example in which the group velocity dispersion produced in the optical fibers 122-1 to 122-n is always set to be negative; however, instead of this, if a compensating member that compensates for the group velocity dispersion in elements other than the optical fibers 122-1 to 122-n, such as the optical systems 106 to 110, is provided, the optical fibers may be selected so that the group velocity dispersion of the optical fibers 122-1 to 122-n themselves is zero, depending on the individual wavelengths of the ultrashort pulsed laser beams emitted from the laser light source 121.

Seventh Embodiment

Figure 13:
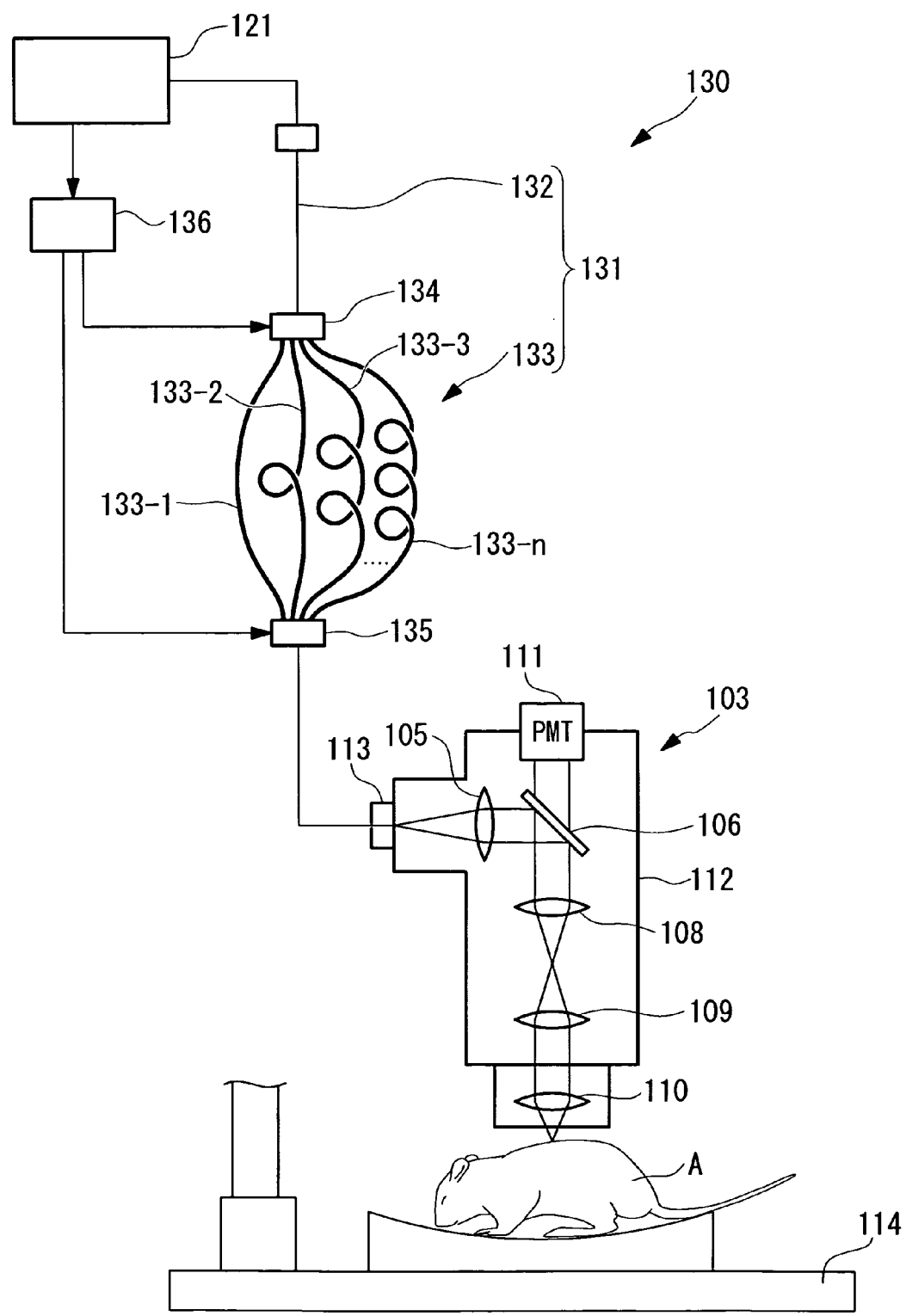
FIG. 13 is an overall structural diagram schematically showing a multiphoton-excitation-type examination apparatus according to a seventh embodiment of the present invention.

Next, a multiphoton-excitation-type examination apparatus 130 according to a seventh embodiment of the present invention will be described below with reference to FIG. 13.

Parts in the description of this embodiment having the same configuration as those in the multiphoton-excitation-type examination apparatus 120 according to the sixth embodiment described above are assigned the same reference numerals, and a description thereof shall be omitted here.

The difference between the multiphoton-excitation-type examination apparatus 130 according to this embodiment and the multiphoton-excitation-type examination apparatus according to the sixth embodiment lies in an optical fiber unit 131.

The optical fiber unit 131 in this embodiment includes a first optical fiber 132 exhibiting negative group velocity dispersion and second optical fibers 133 exhibiting positive group velocity dispersion.

The second optical fibers 133 are formed of a plurality of optical fibers 133-1 to 133-n having different lengths. These optical fibers 133-1 to 133-n are all formed of the same type of optical fiber, with only their lengths varying; they all exhibit positive group velocity dispersion.

Optical switches 134 and 135 are disposed at the two ends of these second optical fibers 133, for selecting different optical fibers 133-1 to 133-n depending on the wavelength of the ultrashort pulsed laser beams emitted by the laser light source 121. In the figure, reference numeral 136 represents a control device that receives wavelength information from the laser light source 121 and outputs switching signals to the optical switches 134 and 135.

With the multiphoton-excitation-type examination apparatus 130 according to this embodiment, having such a configuration, the first optical fiber exhibits negative group velocity dispersion; however, because the amount of group velocity dispersion varies depending on the wavelength of the ultrashort pulsed laser light emitted from the laser light source 121, this variation can be compensated for by selecting one of the second optical fibers 133.

More concretely, the first optical fiber 132 compensates for positive group velocity dispersion in all optical elements except for the first optical fiber 132. Therefore, if the negative group velocity dispersion of the first optical fiber 132 is small, the optical fibers 133-1 to 133-$n$ constituting the second optical fibers 133 are switched, and if the positive group velocity dispersion is small and the negative group velocity dispersion is large, the optical fibers 133-1 to 133-$n$ constituting the second optical fibers 133 are switched so as to increase the positive group velocity dispersion, which allows the overall group velocity dispersion to be made substantially zero.

As a result, it is possible to carry out observation of various fluorescent proteins, such as GFP and RFP, and observation of various fluorescent dyes by switching between single wavelengths, in the same way as in the multiphoton-excitation-type examination apparatus 120 according to the sixth embodiment. Furthermore, there is an advantage in that it is possible to obtain detailed fluorescence images during examination with all wavelengths.

What is claimed is:

1. A laser-based, multiphoton-excitation-type examination apparatus, comprising:
    a laser light source that oscillates ultrashort pulsed laser light;
    an optical fiber that transmits the ultrashort pulsed laser light from the laser light source, the optical fiber having a first end and a second end, the first end being connected to the laser light source;
    a support member;
    a measurement head supported on the support member so as to be movable upwards and downwards and at an angle, the measurement head being connected to the second end of the optical fiber and incorporating an optical system that irradiates a specimen with the ultrashort pulsed laser light transmitted by the optical fiber and that measures fluorescence or reflected light coming from the specimen; and
    a dispersion-compensating member, in the measurement head, that compensates for group velocity dispersion of the ultrashort pulsed laser light irradiated onto the specimen.

2. The multiphoton-excitation-type examination apparatus according to claim 1, wherein the measurement head and the optical fiber are connected in a detachable manner.

3. The multiphoton-excitation-type examination apparatus according to claim 1, further comprising:
    an optical scanning unit, in the measurement head, that scans the ultrashort pulsed laser light transmitted by the optical fiber onto the specimen,
    wherein the dispersion-compensating member is disposed between an end of the optical fiber and the optical scanning unit.

4. The multiphoton-excitation-type examination apparatus according to claim 1, wherein the dispersion-compensating member can be exchanged.

5. The multiphoton-excitation-type examination apparatus according to claim 1, further comprising:
    an adjustment mechanism that adjusts the amount of dispersion-compensation of the dispersion-compensating member.

6. The multiphoton-excitation-type examination apparatus according to claim 1, wherein the dispersion-compensating member is formed of a dispersion-compensating mirror that imparts negative group velocity dispersion.

7. The multiphoton-excitation-type examination apparatus according to claim 6, further comprising:
    a dispersion-imparting member, disposed between the laser light source and the optical fiber, that imparts positive group velocity dispersion to the light introduced into the optical fiber.

8. The multiphoton-excitation-type examination apparatus according to claim 7, wherein the dispersion-imparting member is an acousto-optical device.

9. The multiphoton-excitation-type examination apparatus according to claim 1, further comprising:
    a first dispersion-imparting member, disposed between the laser light source and the optical fiber, that imparts negative group velocity to the light introduced into the optical fiber;
    wherein the dispersion-compensating member is formed of a second dispersion-imparting member that imparts positive group velocity dispersion.

10. The multiphoton-excitation-type examination apparatus according to claim 9, wherein the second dispersion-imparting member is formed of zinc selenide or tellurium oxide crystal.

11. The multiphoton-excitation-type examination apparatus according to claim 1, further comprising:
    an objective unit, disposed opposite the specimen, that is detachable from and attachable to the measurement head; and
    an objective dispersion-compensating unit, disposed in the objective unit, that compensates for the group velocity dispersion of the ultrashort pulsed laser light inside the objective unit.

12. A laser-based, multiphoton-excitation-type examination apparatus, comprising:
    a laser light source that oscillates ultrashort pulsed laser light;
    an optical fiber unit that transmits the ultrashort pulsed laser light from the laser light source; and
    a measurement head incorporating an optical system that irradiates a specimen with the ultrashort pulsed laser light transmitted by the optical fiber unit and that measures fluorescence or reflected light coming from the specimen,
    wherein the laser light source is capable of changing a wavelength of the emitted ultrashort pulsed laser light; and
    the optical fiber unit includes:
        a plurality of optical fibers having different amounts of group velocity dispersion; and
        a fiber switching unit that selects one of the optical fibers to transmit the ultrashort pulsed laser light based on the wavelength of the ultrashort pulsed laser light emitted from the laser light source.

13. The multiphoton-excitation-type examination apparatus according to claim 12, wherein the optical fiber is a photonic-crystal fiber.

14. The multiphoton-excitation-type examination apparatus according to claim 12, wherein the optical fiber unit includes:
- a first optical fiber imparting negative group velocity dispersion;
- a plurality of second optical fibers imparting different amounts of positive group velocity dispersion; and
- a fiber switching unit that selects one of the second optical fibers to transmit the ultrashort pulsed laser light transmitted by the first optical fiber based on the wavelength of the ultrashort pulsed laser light emitted from the laser light source.

15. The multiphoton-excitation-type examination apparatus according to claim 14, wherein the second optical fibers are formed of a plurality of optical fibers of the same type and having different lengths.

* * * * *